(12) United States Patent
He et al.

(10) Patent No.: US 8,476,588 B2
(45) Date of Patent: Jul. 2, 2013

(54) METHOD OF ELECTRON DIFFRACTION TOMOGRAPHY

(75) Inventors: Haifeng He, Rockville, MD (US); Andreas Voigt, Eindhoven (NL)

(73) Assignee: FEI Company, Hillsboro, OR (US)

( * ) Notice: Subject to any disclaimer, the term of this patent is extended or adjusted under 35 U.S.C. 154(b) by 195 days.

(21) Appl. No.: 13/174,490

(22) Filed: Jun. 30, 2011

(65) Prior Publication Data

US 2012/0001068 A1 Jan. 5, 2012

(30) Foreign Application Priority Data

Jun. 30, 2010 (EP) ..................................... 10167891

(51) Int. Cl.
*G01N 23/00* (2006.01)
*G21K 7/00* (2006.01)

(52) U.S. Cl.
USPC ........... 250/307; 250/306; 250/305; 250/310; 250/311

(58) Field of Classification Search
USPC .................................. 250/305–307, 310, 311
See application file for complete search history.

(56) References Cited

U.S. PATENT DOCUMENTS

| | | | |
|---|---|---|---|
| 8,247,769 B2 * | 8/2012 | Zewail | 250/311 |
| 8,253,099 B2 * | 8/2012 | Nicolopoulos et al. | 250/307 |
| 2011/0284744 A1 * | 11/2011 | Zewail et al. | 250/307 |

FOREIGN PATENT DOCUMENTS

| | | |
|---|---|---|
| EP | 1635374 | 3/2006 |
| WO | 2010052289 | 5/2010 |

OTHER PUBLICATIONS

Dronyak, Roman, et al., "Electron coherent diffraction tomography of a nanocrystal," Applied Physics Letters, Jun. 3, 2010, pp. 21907-1-21907-3, vol. 96.
Kolb, U., et al., "Towards automated diffraction tomography: Part I—Data acquisition," Ultramicroscopy, Feb. 25, 2007, pp. 507-513, vol. 107, No. 6-7.
Kolb, U., et al., "Towards automated diffraction tomography: Part II—Cell parameter determination," Ultramicroscopy, Jul. 1, 2008, pp. 763-772, vol. 108, No. 8.
Miot, Jennyfer, et al., "Iron biomineralization by anaerobic neutrophilic iron-oxidizing bacteria," Geochimica et Cosmochimica Acta, Feb. 1, 2009, pp. 696-711, vol. 73, No. 3.
Anonymous. "High-Resolution Microscopy Meeting," Conference Proceedings of SCANDEM 2010, Jun. 8, 2010-Jun. 11, 2010, 36 pages.
"Collaborative Computational Project No. 14," http://www.ccp14.ac.uk/about.htm., retrieved Jun. 30, 2010.

* cited by examiner

*Primary Examiner* — Jack Berman
*Assistant Examiner* — Meenakshi Sahu
(74) *Attorney, Agent, or Firm* — Scheinberg & Associates, PC; Michael O. Scheinberg

(57) ABSTRACT

The invention relates to a method for electron diffraction tomography in a Transmission Electron Microscope. Known methods involve using Scanning Transmission Electron Microscope, and use the scanned beam for STEM diffraction. The invention proposes to form the diffraction patterns with a stationary beam with a diameter slightly larger than the crystal, as a result of which a TEM without STEM unit can be used. Finding the crystal is done in TEM mode. Advantages of the method according to the invention are: a TEM without scanning unit can be used, and the diffraction volume is not depending on the orientation of the crystal, as the whole crystal is illuminated while obtaining the diffraction pattern.

17 Claims, 3 Drawing Sheets

METHOD OF ELECTRON DIFFRACTION TOMOGRAPHY

TECHNICAL FIELD OF THE INVENTION

The invention relates to a method of determining the crystallographic structure of a crystal by electron diffraction tomography using an electron microscope.

BACKGROUND OF THE INVENTION

This method is known from "Towards automated diffraction tomography: Part I-Data acquisition", U. Kolb et al., Ultramicroscopy 107 (2007) 507-513.

There is great interest in determining the structure of macro-molecules, such as catalysts, proteins, viruses, DNA and RNA. The knowledge is of importance for understanding how e.g. proteins operate, how to produce, for example, more effective medicaments, enzymes, etc., and for example to understand why certain illnesses occur.

A group of techniques known as crystallography is used to determine the structure of molecules, of which X-ray crystallography is the most well-known. Here a multitude of diffraction patterns is recorded by irradiating a crystal by a beam of X-rays, and a diffraction pattern of said beam is recorded. A disadvantage of X-ray crystallography is that the size of the crystals must be rather large, e.g. 0.1 μm or more, because the interaction between the crystals and the X-ray beam is small. For many inorganic crystals this is not a problem, as these can easily be grown to a size of 0.1 μm or more, but it proves to be extremely difficult to grow crystals of e.g. proteins to such a size. X-ray diffraction is thus less suited for determining the structure of e.g. proteins.

The interaction between a beam of accelerated electrons, as used in e.g. an electron microscope, and the atoms of a crystal is much larger than when using X-rays. Therefore diffraction patterns of nano-crystals, with a diameter of less than 1 μm down to several nm, can be recorded with, for example, a transmission electron microscope (TEM).

In the known method described by U. Kolb, three-dimensional (3D) diffraction data are collected by manually tilting a crystal around a selected crystallographic axis and recording a set of diffraction patterns (a tilt series) at various crystallographic zones. In a second step, diffraction data from these zones are combined into a 3D data set and analyzed to yield the desired structure information. It is noted that data collection can be performed automatically. This involves a software module for a TEM enabling automated diffraction pattern collection while tilting around the goniometer axis. Kolb then proceeds to describe such a software module for a TEM, combining Scanning Transmission Electron Microscopy (STEM) imaging with diffraction pattern acquisition in nanodiffraction mode. It allows automated recording of diffraction tilt series from nanoparticles with a size down to 5 nm.

In the introduction Kolb teaches that the diffraction patterns can be recorded by illuminating the crystal with area selecting, the so-named Selected Area Electron Diffraction (SAED) technique, in which an aperture downstream of the diffraction plane is used to limit the part (the area) of the sample contributing to the diffraction pattern. The beam can be a convergent, focused beam (CBED), a substantially parallel beam, or any convergence angle therein between. Parallel illumination can be obtained by Köhler illumination. Alternatively a small aperture, known as the C2 aperture, can be used to decrease the beam diameter to a few nanometers while keeping the beam almost parallel. Kolb proceeds to describe that working in TEM mode with a small beam of typically 50 nm diameter makes it nearly impossible to position the beam with any degree of accuracy on a crystal that is larger than the beam. Therefore the position of the crystal is determined in STEM mode.

It is noted that Kolb mentions that in principle the diffraction patterns can be recorded using a more or less parallel beam, but fails to give an example of this. On the contrary, she proceeds showing Convergent Beam Electron Diffraction, and e.g. at page 509 of her article, lower right corner, says that the diffraction pattern is not focused in the back-focal plane.

A disadvantage of said method is that not all TEM's are equipped with a scanning unit, as a result of which not all TEM's can operate in STEM mode.

There is a need for a method that can be performed on an instrument that is not equipped with a scanning unit in order to operate in STEM mode.

SUMMARY OF THE INVENTION

The invention describes a method for electron diffraction tomography in a Transmission Electron Microscope. Known methods involve using Scanning Transmission Electron Microscope, and use the scanned beam for STEM diffraction. The invention proposes to form the diffraction patterns with a stationary beam (200) with a diameter slightly larger than the crystal, as a result of which a TEM without STEM unit can be used. Finding the crystal is done in TEM mode. Advantages of the method according to the invention are: a TEM without scanning unit can be used, and the diffraction volume is not depending on the orientation of the crystal, as the whole crystal is illuminated while obtaining the diffraction pattern.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The invention is now elucidated on the basis of figures, where identical reference numerals indicate corresponding elements.

DETAILED DESCRIPTION OF PREFERRED EMBODIMENTS

Figure 1:
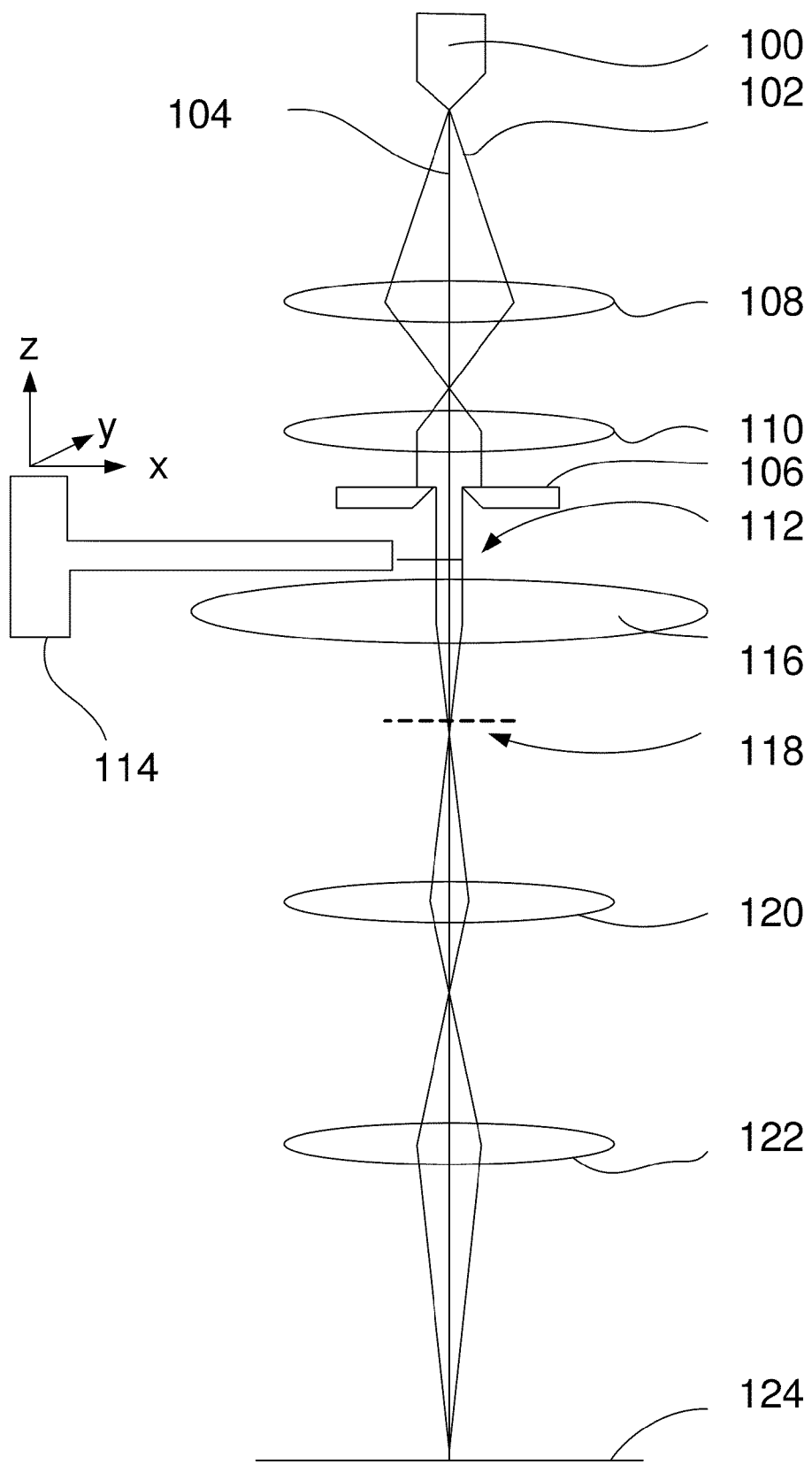
FIG. 1 depicts schematically optical elements for a TEM performing the method according to the invention.

The method according to the invention is characterized in that the beam used for recording the diffraction patterns is a substantially parallel beam having a diameter larger than the size of the crystal.

By using a beam with a diameter larger than the crystal, and keeping this beam stationary with respect to the crystal while recording the diffraction pattern, the TEM used does not need to be equipped with a scanning unit for scanning the beam over the crystal.

As the diameter of the beam is larger than the diameter of the crystal, the interaction volume, or scattering volume, also known as diffraction volume is the volume of the crystal itself, and thus for all tilt angles the same. This eases the normalization and post-processing otherwise needed when recording the diffraction patterns and/or analyzing the recorded diffraction patterns.

In an embodiment of the method according to the invention the centering of the crystal with respect to the beam involves shifting the beam and/or mechanically moving the crystal.

By moving the beam over the sample, e.g. by applying a magnetic or electrostatic field, the beam can be positioned over the crystal. For large displacements also a mechanical movement of the sample can be performed.

In a preferred embodiment of the method according to the invention the beam used for recording the diffraction pattern is a substantially parallel beam.

When tilting the sample the position of the sample will often change, which can be corrected by shifting the beam. When using a parallel beam tilting of the sample and/or shifting the beam does not shift the origin of the diffraction pattern, nor will it distort the diffraction pattern.

This is advantageous when compared to the work described by U. Kolb, where the diffraction pattern is formed with a convergent beam, resulting in disks rather than spots in the back focal plane of the objective lens. For both the convenience of later stage data processing and more importantly to separate each reflections clearly (for macro-molecular crystals, the reflections can be very dense and disks are easily overlapped with each other), an extra step has to be taken to re-focus the disks into spots by any of the three methods:
1). vary the current of the objective lens;
2). vary the current of the projection system;
3). vary the current of a third lens, called a diffraction lens on FEI microscopes. The consequence is that the diffraction pattern will shift with the beam shift. This is also acknowledged in the work by U. Kolb in page 509 and 510.

It is noted that other methods of crystallography are known, such as, but not necessarily limited to, X-ray single crystal diffraction, X-ray powder diffraction, 2D electron diffraction, and Precession Electron Diffraction. X-ray single crystal diffraction methods have as draw-back the large crystals needed, as discussed previously.

X-ray powder diffraction method has the difficulty of offering a unique or reliable solution, that is: it is difficult or impossible to determine a unique crystallographic structure. This is due to the fact that rotational information in the diffraction pattern is lost as a result of the diffraction patterns of a multitude of crystals.

2D electron diffraction demands a very special type of crystal (a 2D monolayer) which is very difficult to produce.

Precession Electron Diffraction demands a TEM capable of precession (rotating the beam in a cone, the center of the cone on the crystal) and cancelling the rotation of the beam again after passing the crystal, so that a stationary diffraction pattern is formed. This demands special TEM's.

Therefore all these other methods have drawbacks with regard to the limitations of the method itself, the crystals, or the instruments used.

In an embodiment of the method according to the invention the crystal has a largest diameter less than 10 μm, more specifically less than 1 μm, most specifically less than 100 nm. Making such small crystals is much easier than making the large crystals needed in, for example, X-ray diffraction, typically having sizes of 100 μm or more. This especially holds for proteins.

In yet another embodiment of the method according to the invention the crystal is a crystal of macro-molecules from the group of catalysts, proteins, viruses, DNA and RNA.

Identification of the crystallographic structure of e.g. proteins is very much in the interest, both for industrial processes (e.g. for synthesizing enzymes) and in healthcare (e.g. for synthesizing drugs)

In still another embodiment of the method according to the invention a multitude of crystals is identified, and for each tilt angle a multitude of diffraction patterns is recorded, each diffraction pattern associated with one of the crystals.

Recording diffraction patterns for a number of crystal using the above mentioned method with identical crystallographic structure results in better results due to a better signal-to-noise ratio, and because more crystallographic directions are probed, as each of the crystals is likely to have a different orientation with respect to the beam. This can be realized with one tilt series, and therefore with a limited amount of (mechanical) steps for tilting the crystals.

It is noted that in this method for each of the crystals a series of diffraction patterns is made and analyzed. Therefore this method differs from analyzing poly-crystalline material. It is further noted that this method can be used to acquire data from two or more crystals with different crystallographic structure and/or composition as well, and analyze the two or more sets of data separately. This results in a higher throughput, as only one mechanical tilt series is made, and also the centering can be realized more efficiently by determining the position of one crystal or one set of features (the mutual positions known), thus saving acquisition time.

In still another embodiment of the method according to the invention the electron microscope is a cryo electron microscope and the diffraction patterns are recorded while the sample is at a cryogenic temperature.

The environment within an electron microscope is a harsh environment, with high levels of radiation and vacuum. As known to the person skilled in the art the "lifetime" of molecules at cryogenic temperatures is much larger than when the molecules are studied at room temperature. It is noted that TEM's equipped to operate at liquid nitrogen temperature and/or liquid helium temperature are readily available.

In still another embodiment the sample is mounted on a tilt holder from the group of single-tilt holders and double-tilt holders, and the tilting is the result of tilting the tilt holder.

To position a sample in a TEM the sample is normally mounted on a grid, for example a copper grid with a diameter of 3.05 mm, and said grid is in turn mounted on a holder. The holder is then inserted in a so-named goniometer, which seals against the holder, while simultaneously enabling movement of the sample at the sample position. Some holders enable (in cooperation with a goniometer) tilt, some enable tilt in two directions. Also holders enabling cryogenic use, and/or enabling heating, etc. are known. For the analysis needed here a single tilt holder suffices.

It is noted that the holder used is typically a side-entry rigid holder that is tilted by the so-named goniometer. The goniometer is typically capable to shift the holder in the x, y and z direction and rotate the holder in one direction, It is further noted that often a so-called tomo-holder is used, that is essentially a single tilt holder equipped for large tilt angles without touching the pole pieces of the (magnetic) lenses of the microscope and having provisions for not intercepting the incoming and outgoing beam of electrons even at a high tilt angle (typically 60 to 80 degrees). It is mentioned that holders of other types, such as top loading holders, or double tilt holders, are known, as well as holders where the rotation/translation of the sample is realized by, for example, piezomotors at the tip of the holder.

In still another embodiment the diffraction pattern is formed using an objective lens and during at least part of the tilt positions the position of the crystal is centered with respect to the beam and the objective lens using a model of the movement of the tilt holder with respect to the beam and said objective lens, as a result of which the crystal is not exposed to electrons during the centering of the crystal.

If the accuracy/reproducibility of the position of the holder and the goniometer are sufficient, the crystal can be positioned at least part of the time by 'dead-reckoning'. This minimizes the exposure of the crystal to electrons, and thus minimizes damage during centering of the crystal.

In still another embodiment centering the crystal involves imaging at least part of the sample using a beam of electrons.

The TEM is capable of imaging the sample with great accuracy, and thus the position of the crystal can be determined with high precision with respect to the beam.

In a further embodiment the imaging of the sample involves imaging the crystal.

By imaging the crystal, usually at a relatively low magnification which limits the dose to the crystal, its position is recorded with high accuracy. It is noted that the electron dose per unit area need not be large, and thus the amount of electrons to which the crystal is exposed can be low.

In another embodiment the position of one or more features in the sample relative to the crystal is determined before making the tilt series, and the imaging of the sample involves imaging the one or more features, and the position of the features is used to center the crystal.

Here first the position of the crystal with respect to one or more features is determined. During the tilt series the position of the crystal can now be derived by determining the position of the one or more features. In this way the crystal is not exposed to electrons while centering, It is noted that when one feature is used to determine the position of the crystal preferably both the crystal of interest and the feature are located at or near the tilt axis, but that when two or more features are used, neither the features nor the crystals need to be located on the tilt axis (although the position with respect to the tilt axis should be known to make a model describing how the features and crystal move due to the rotation.

In still another embodiment the diameter of the beam used for centering the crystal differs from the diameter of the beam used for recording a diffraction pattern.

Preferably the beam diameter for the centering is larger than the beam diameter used for diffraction, so that during centering a large field of view is available, while the beam used for recording the diffraction pattern is only slightly larger than the crystal.

In still another embodiment the crystal is during the recording of the tilt series exposed to a dose of less than $10^5$ electrons/nm$^2$ By exposing the crystal to a dose less than $10^5$ electrons/nm$^2$ for the sum of all the tilt positions in the tilt series (the accumulated dose during the whole series), the damage to the crystal is limited. See also the publication by Kolb.

In still another embodiment the crystal is during the recording of the tilt series exposed to a dose rate of less than 300 electrons/(nm$^2$ s).

As mentioned by Kolb, also the dose rate needs to be controlled to a low value of, for example, less than 300 electrons/(nm$^2$ s).

FIG. 1 depicts schematically optical elements for a TEM performing the method according to the invention.

FIG. 1 shows an electron source 100 for producing a beam 102 of energetic electrons with an energy of, e.g. between 50 and 400 keV, along electron- optical axis 104. It is noted that in reality the position where the beam is focused (shows cross-over's) differs from the sketched positions—and thus angular and linear magnifications differ—, but these cross-over's are used to limit the beam diameter. It is further noted that electron microscopes using lower and higher beam energies are known. It is noted that one or more lenses between the electron source and the aperture may be present, as well as alignment coils to center the beam on the axis. Condenser lenses 108 and 110 are used to form a beam on sample position 112. The diameter of the beam at the sample position is governed by aperture 106. A sample mounted on sample positioning unit, the so-named goniometer 114, is placed on said sample position, the goniometer enabling positioning the sample on the sample position along any of axis x, y, z and rotating the sample along the x-axis. Objective lens 116 with a back-focal plane 118 images the sample, and projection lenses 120 and 122 form an enlarged image on imaging plane 124, which may be a fluorescent screen, or the plane where a camera system resides.

It is noted that the sample may be immersed in the (magnetic) field of the objective lens 116. In that case the objective lens can be thought to be split in two parts, one cooperating with the condenser lenses 106 and 108 to illuminate the sample and a second part cooperating with the projection lenses 118 and 120 forming an image.

A TEM can image a sample in different ways. Two important modes are:

Diffraction mode: in diffraction mode the sample is illuminated with a, preferably parallel, beam of electrons, as a result of which a diffraction pattern is formed in the back-focal plane of the objective lens (all parallel rays are focused in this plane, the position where the focus is formed dependent only on the angle with which the electrons leave the sample plane), and the projection lenses form an enlarged image of this back-focal plane on the image plane.

TEM imaging mode: in TEM imaging mode the sample is illuminated with a beam of electrons (that may be a parallel beam). The projection lenses do not image the back-focal plane of the objective lens, but the sample plane on the imaging plane (for example a florescent screen or a camera). The image is formed by intensity variation resulting from a part of the electrons being absorbed in the sample, and electrons diffracted (scattered) in the sample interfering with electrons that pass the sample unhindered.

It is noted that a Scanning Transmission Electron Microscope resembles a TEM, but is additionally equipped with deflection coils between lens 108 and the sample, and focuses the beam on the sample. By then scanning the focused beam over the sample with these deflection coils, a scanning image is made, using detectors placed under the sample (at the side removed from the electron source).

Figure 2:
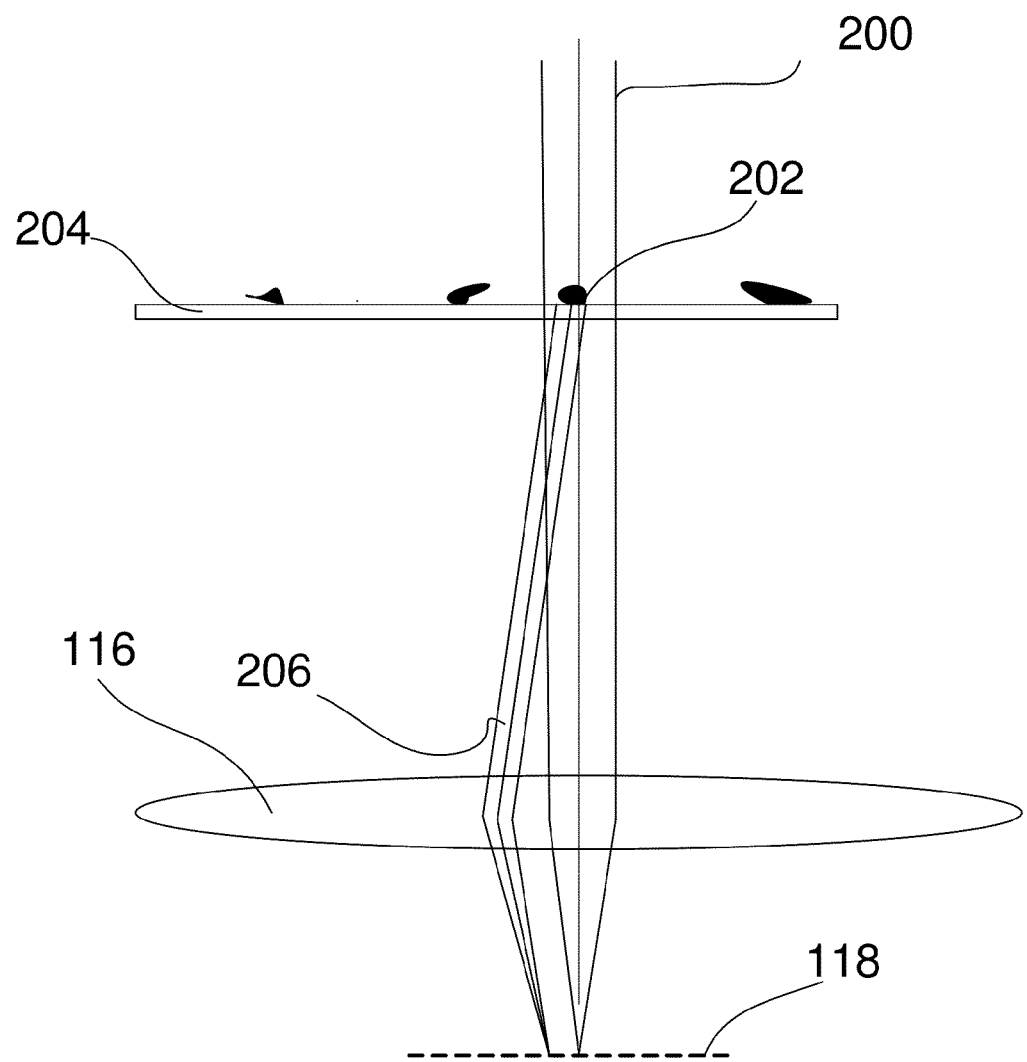
FIG. 2 depicts schematically the rays in diffraction mode.

FIG. 2 schematically shows the ray diagram near the sample in diffraction mode.

FIG. 2 shows a parallel beam of electrons 200 impinging on a sample 204. The sample comprises a crystal 202, causing the beam 200 to split in an undiffracted beam and a diffracted beam 206. Objective lens 116 focuses both the undiffracted and the diffracted beam in diffraction plane 118, as both beams are parallel beams.

It is noted that, for perfectly parallel beams and an objective lens without lens aberrations, the foci formed in diffraction plane 118 are points. In reality the spots have a small but finite diameter due to beam convergence/divergence, mainly as a result of the finite diameter of the source.

As is clear from FIG. 2, a beam with a diameter larger than the crystal results in a constant diffraction volume: the volume of the complete crystal.

It is noted that for the method of the invention normally some adjustments are made before recording the tilt series. These are:

the so-named camera-length is determined. This parameter describes the magnification of the diffraction plane to the image plane (camera or screen).

alignment of the beam to illuminate the same area on the sample both when recording a diffraction pattern and when imaging the Image/beam shift has to be calibrated at each Magnification.

the position of the tilt axis of the stage has to be determined

Figure 3:
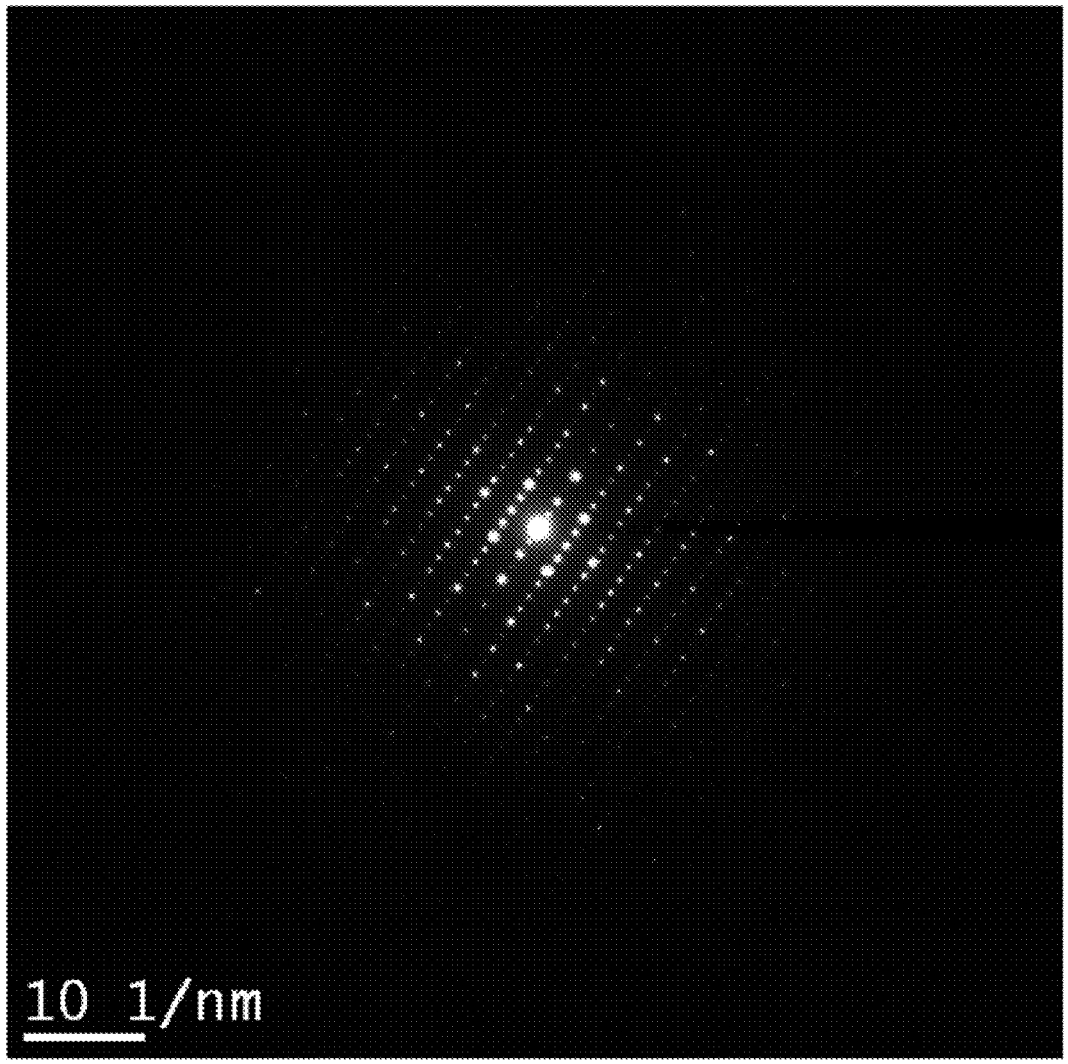
FIG. 3 depicts a diffraction pattern.

FIG. 3 shows a diffraction pattern.

Clearly a strong central peak is visible, as well as a multitude of sub-peaks. The central peak is the result of the focusing of the electrons that pass through the sample unhindered, and each of the sub-peaks corresponds with electrons that are scattered under a specific angle with respect to the incoming beam.

The more complex a crystal is (that is: the more atoms there are in a unit cell), the more complex the diffraction pattern is: the more spots are visible. Also: the more complex a crystal is, the more weak spots are present.

It is noted that this diffraction pattern shows symmetry around the central spot, but that for most tilt angles the diffraction pattern does not show symmetry.

It is noted that, for example, "Collaborative Computational Project No. 14" (CCP14) resulted in a suite of software packages to analyze diffraction patterns, see the CCP14 website http://www.ccp14.ac.uk/about.htm. This and other packages are well known to the person skilled in the art.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of determining the crystallographic structure of a crystal by electron diffraction tomography using an electron microscope, the electron microscope equipped to irradiate the crystal with a beam of electrons, the method comprising:

providing a sample with one or more crystals therein,
identifying a crystal to be analyzed on the sample,
recording a diffraction tilt series of the crystal by repeatedly tilting the sample to a known tilt angle with respect to the beam,
centering the crystal with respect to the beam, and
recording a diffraction pattern of the crystal at said tilt angle, and
determining the crystallographic structure by analyzing the recorded diffraction patterns,
in which while recording the diffraction image, the beam is kept stationary with respect to the crystal, and the beam has a diameter larger than the diameter of the crystal.

2. The method of claim 1 in which the centering of the crystal with respect to the beam involves shifting the beam and/or mechanically moving the crystal.

3. The method of claim 1 in which the beam used for recording the diffraction pattern is a substantially parallel beam.

4. The method of claim 1 in which the crystal has a largest diameter less than 10 μm.

5. The method of claim 1 in which the crystal is a crystal of macro-molecules from the group of catalysts, proteins, viruses, DNA and RNA.

6. The method of claim 1 in which a multitude of crystals is identified, and for each tilt angle a multitude of diffraction patterns is recorded, each diffraction pattern associated with one of the crystals.

7. The method of claim 1, in which the electron microscope is a cryo-electron microscope and the diffraction patterns are recorded while the sample is at a cryogenic temperature.

8. The method of claim 1 in which the sample is mounted on a tilt holder from the group of single-tilt holders and double-tilt holders, and the tilting of the sample is the result of tilting the tilt holder.

9. The method according to claim 8 in which the diffraction pattern is formed using an objective lens and during at least part of the tilt positions the position of the crystal with respect to the beam and the objective lens is centered using a model of the movement of the tilt holder with respect to the beam and said objective lens, as a result of which the crystal is not exposed to electrons during the centering of the crystal.

10. The method according to claim 1 in which the centering of the crystal involves imaging at least part of the sample using a beam of electrons.

11. The method of claim 10 in which imaging the sample using a beam of electrons involves imaging the crystal.

12. The method of claim 10 in which before making the tilt series the position of one or more features in the sample relative to the position of the crystal is determined, and in which imaging the sample using a beam of electrons involves imaging the one or more features, and the position of the one or more features is used to centre the crystal, as a result of which the crystal is not exposed to electrons during the centering of the crystal.

13. The method of claim 10 in which the diameter of the beam used for centering the crystal differs from the diameter of the beam used for recording a diffraction pattern.

14. The method of claim 1 in which the crystal during the recording of the tilt series is exposed to a dose of less than $10^5$ electrons/nm$^2$.

15. The method of claim 1 in which the crystal during the recording of the tilt series is exposed to a dose rate of less than 300 electrons/(nm$^2$s).

16. The method of claim 1 in which the crystal has a largest diameter less than 1 μm.

17. The method of claim 1 in which the crystal has a largest diameter less than 100 nm.

* * * * *